US008110999B2

(12) United States Patent
Ikeda (10) Patent No.: US 8,110,999 B2
(45) Date of Patent: Feb. 7, 2012

(54) LIGHT SOURCE APPARATUS

(75) Inventor: Yoshinori Ikeda, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 12/836,040

(22) Filed: Jul. 14, 2010

(65) Prior Publication Data

US 2010/0277087 A1 Nov. 4, 2010

Related U.S. Application Data

(63) Continuation of application No. PCT/JP2008/072136, filed on Dec. 5, 2008.

(30) Foreign Application Priority Data

Jan. 23, 2008 (JP) .................................. 2008-012488

(51) Int. Cl.
*H05B 41/16* (2006.01)
*H05B 39/04* (2006.01)

(52) U.S. Cl. ....................................... 315/246; 315/308

(58) Field of Classification Search ................... 315/246, 315/247, 248, 291, 307, 308, 310
See application file for complete search history.

(56) References Cited

U.S. PATENT DOCUMENTS

| 5,489,831 | A | * | 2/1996 | Harris | 318/701 |
| 7,253,577 | B2 | * | 8/2007 | Campbell et al. | 318/563 |
| 7,641,364 | B2 | * | 1/2010 | Abbondanzio et al. | 362/295 |
| 2003/0218723 | A1 | | 11/2003 | Yamanaka | |
| 2004/0090602 | A1 | | 5/2004 | Imade | |
| 2004/0125344 | A1 | | 7/2004 | Matsui | |

FOREIGN PATENT DOCUMENTS

| JP | 2003-344948 | 12/2003 |
| JP | 2004-071393 | 3/2004 |
| JP | 2004-199024 | 7/2004 |

OTHER PUBLICATIONS

International Search Report issued in International Application No. PCT/JP2008/072136.

* cited by examiner

*Primary Examiner* — Douglas W Owens
*Assistant Examiner* — Minh D A
(74) *Attorney, Agent, or Firm* — Volpe and Koenig P.C.

(57) ABSTRACT

The light source apparatus is provided with a plurality of light source device disposed in the form of a ring and that emit illumination light toward the central axis of the ring by being lit in a sequential pulsed fashion; a light-guide portion having a light entrance surface rotatably disposed on the central axis and on which the illumination light emitted from the light source devices is incident, and a reflecting surface that reflects the incident illumination light in the direction along the central axis; and a driving device that controls a pulsed-lighting phase range. The driving device controls the pulsed-lighting phase range (W) such that, when the pulsed-lighting phase range (W) is shorter than a maximum-pulse phase range (M), a preceding light-out phase range (F) and a succeeding light-out phase range (R) are provided before and after the pulsed-lighting phase range (W) in the maximum-pulse phase range (M).

6 Claims, 4 Drawing Sheets

LIGHT SOURCE APPARATUS

CROSS REFERENCE TO RELATED APPLICATIONS

This is a continuation of International Application PCT/JP2008/072136, with an international filing date of Dec. 5, 2008, which is hereby incorporated by reference herein in its entirety. This application claims the benefit of Japanese Patent Application No. 2008-012488, the content of which is incorporated herein by reference.

FIELD OF THE INVENTION

The present invention relates to light source apparatuses and, more particularly, to a light source apparatus that guides light emitted from a plurality of light-emitting devices, which emit pulsed light, to an illumination region.

DESCRIPTION OF RELATED ART

In the related art, with regard to a light source apparatus utilizing light-emitting devices such as LEDs (Light Emitting Diodes) and so forth, there is a known method in which a plurality of light-emitting devices are lit in a sequential pulsed fashion in order to increase the light level of the emitted light. By emitting the pulsed light with this method, the light level of the light emitted becomes higher compared with a method in which the light-emitting devices are continuously lit.

With the method employing sequential pulsed lighting, in order to output the light emitted from the light-emitting devices to an illumination target efficiently, it is necessary to use a light-guide member, such as a reflector or an optical lens, and various light-guide methods have been proposed (for example, see Patent Citation 1).

Patent Citation 1 describes an illumination apparatus provided with a plurality of light-emitting devices disposed so as to be capable of moving and a light-guide optical system that guides the light emitted from the light-emitting devices to an illuminated region; an illumination apparatus provided with light-emitting devices that are disposed in the form of a ring and that emit light toward the center of the ring and a light-guide optical system that rotates about the central axis of the ring and that guides the light emitted from the light-emitting devices to the illuminated region; and so forth.

With the illumination apparatuses described in Patent Citation 1, the light is efficiently output toward the illuminated region by emitting the light from the light-emitting devices at the timing at which the light-guide optical system and the light-emitting devices are disposed facing each other.

In the case of such illumination apparatuses, methods that have generally been considered for adjusting the light level of the light emitted toward the illumination region include a method in which the pulse width of the light emitted from the light-emitting devices is adjusted, a method in which a current value to be supplied to the light-emitting devices is adjusted, and so forth.

Patent Citation 1

Japanese Unexamined Patent Application, Publication No. 2004-71393

BRIEF SUMMARY OF THE INVENTION

However, in the method in which the current value to be supplied to the light-emitting devices is changed, there has been a problem in that the color temperature of the light output toward the illumination region is changed. In other words, since the light-emitting devices have a characteristic whereby the color temperature of the emitted light changes in accordance with the current value supplied thereto, in the method in which the light level is adjusted by changing the current value, there has been a problem in that the color temperature of the light to be output is changed.

On the other hand, in the method in which the pulse width is changed, there has been a problem in that the fluctuation of the light level of the light output toward the illumination region becomes large. In other words, if the pulse width of the emitted light becomes shorter, the variation between the light-emission timing of the light-emitting devices and the rotation phase of the light-guide optical system becomes relatively larger, and the percentage of the light escaping from the light-guide optical system becomes higher. In other words, there has been a problem in that, since the rate of jitter becomes higher, the fluctuations of the light level become large depending on the light emission cycle, and the fluctuation is perceived as a flickering.

The present invention has been conceived to overcome the problems described above, and an object thereof is to provide a light source apparatus capable of outputting light with a high light level stably and efficiently.

In order to achieve the object described above, the present invention employs the following solutions.

The present invention provides a light source apparatus comprising a plurality of light source devices that are disposed in the form of a ring and that emit illumination light toward the central axis of the ring by being lit in a sequential pulsed fashion; a light-guide portion having a light entrance surface that is rotatably disposed on the central axis and on which the illumination light emitted from the light source devices is incident, and a reflecting surface that reflects the incident illumination light in the direction along the central axis; and driving device that controls a pulsed-lighting phase range that is a period during which the light source devices are lit according to the rotation phase of the light-guide portion; wherein the driving device controls the pulsed-lighting phase range such that, when the pulsed-lighting phase range is shorter than a maximum-pulse phase range, which is the longest period during which the illumination light emitted from the light source devices is incident on the light entrance surface, a preceding light-out phase range and a succeeding light-out phase range, which are periods during which the light source devices are turned off, are provided before and after the pulsed-lighting phase range in the maximum-pulse phase range.

According to the present invention, by controlling the pulsed-lighting phase range, it is possible to adjust the light level of the illumination light emitted from the light-guide portion by adjusting the period during which the illumination light is emitted from the light source devices. Therefore, in comparison with a method in which current value to be supplied to the light source devices is adjusted, a change of color temperature of the illumination light emitted is suppressed.

Furthermore, since the periods during which the light source devices are turned off are ensured before and after the period during which the illumination light is emitted, even if the pulsed-lighting phase range is shortened to shorten the period during which the illumination light is emitted from the light source devices, the illumination light emitted from the light source devices is incident on the light entrance surface of the light-guide portion. In other words, even if a variation is caused between the rotation phase of the light-guide portion and the phase with which the illumination light is emitted in the light source device, the above-described variation is absorbed by the light-out period, and therefore, the illumination light emitted from the light source device is incident on the light entrance surface.

Since pulsed illumination light is emitted from the light source devices, compared with the case where the illumination light is emitted from the light source devices steadily, illumination light with a high light level can be achieved. Furthermore, a plurality of light source devices are provided and the emitted illumination light is guided to an illuminated region by the light-guide portion; therefore, illumination light with a high light level can be achieved continuously.

In the invention described above, it is preferred that the driving device controls the pulsed-lighting phase range such that the preceding light-out phase range and the succeeding light-out phase range have substantially equal widths.

By doing so, the light-out periods of substantially equal duration are ensured before and after the period during which the illumination light is emitted. Therefore, the illumination light emitted from the light source device is incident on the light entrance surface whether the variation between the rotation phase of the light-guide portion and the phase with which the illumination light is emitted in the light source device is toward the advanced side of the emission phase of the illumination light or toward the delayed side of the emission phase of the illumination light.

In the invention described above, it is preferred that the driving device controls the pulsed-lighting phase range such that, when the light-guide portion is rotated under the condition where one of the light source devices is made to emit light continuously, a phase of the center of gravity of the light level related to the change of the light level of the illumination light emitted from the light-guide portion becomes substantially the center of the maximum-pulse phase range.

By doing so, the light-out periods of substantially equal duration are ensured before and after the period during which the illumination light is emitted.

In other words, since the light entrance surface of the light-guide portion passes in front of the light source devices continuously emitting light, the light level of the illumination light emitted from the light-guide portion changes depending on the rotation phase of the light-guide portion. By setting the phase corresponding to the maximum value of the light level at this time as the central phase of the maximum-pulse phase range, or, by setting the phase corresponding to the center of gravity of the area of the light level as the central phase of the maximum-pulse phase range, it is possible to set the preceding light-out phase range and the succeeding light-out phase range to substantially equal widths.

In the invention described above, it is preferred that the driving device controls the pulsed-lighting phase range such that a phase with which the center of the light entrance surface and the center of the exit surface of the illumination light of the light source device are matched becomes a central phase of the pulsed-lighting phase range.

By doing so, since the time at which the center of the light entrance surface and the center of the above-described light exit surface match becomes the center of the period during which the illumination light is emitted from the light source device, light-out periods of substantially equal duration are ensured before and after the period during which the illumination light is emitted.

In the invention described above, it is preferred that the driving device controls the pulsed-lighting phase range such that the succeeding light-out phase range becomes longer than the preceding light-out phase range.

By doing so, a succeeding light-out period after the pulsed-lighting phase period during which the illumination light is emitted becomes longer than a preceding light-out period before the pulsed-lighting phase period. Therefore, even when there is a persistent period during which the illumination light is emitted from the light source device even after the supply of the current to the light source device has been blocked, it becomes easier for the illumination light related to the persistent period to be made incident on the light entrance surface.

In the invention described above, it is preferred that an optical sensor that detects the light level of illumination light emitted from the light-guide portion is provided, wherein the driving device controls the pulsed-lighting phase range such that the light level detected by the optical sensor becomes the maximum.

By doing so, since the pulsed-lighting phase range is controlled on the basis of the light level detected by the optical sensor, regardless of the emission characteristics of the illumination light by the light source devices, it is possible to maximize the light level of the illumination light emitted from the light-guide portion.

In other words, by performing control on the basis of the light level detected by the optical sensor, it is possible to set the preceding light-out phase range and the succeeding light-out phase range before and after the pulsed-lighting phase range. Therefore, it is possible to make the illumination light emitted from the light source devices incident on the light entrance surface of the light-guide portion reliably.

The light source apparatus according to the present invention affords an advantage in that it is possible to adjust the light level of the emitted illumination light and stably output illumination light with a high light level by controlling the pulsed-lighting phase range; and to absorb the variation between the rotation phase of the light-guide portion and the emission phase of illumination light to output the illumination light efficiently by ensuring light-out phase ranges before and after the pulsed-lighting phase range.

EXPLANATION OF REFERENCE

1: light source apparatus
2: LED (light source device)
3: light-guide rod (light-guide portion)
4: reflecting prism (light-guide portion)
9: optical sensor
15: phase adjuster (driving device)
31: light entrance surface
51: reflecting surface W: pulsed-lighting phase range
M: maximum-pulse phase range
F: preceding light-out phase range
R: succeeding light-out phase range

DETAILED DESCRIPTION OF THE INVENTION

First Embodiment

A first embodiment of the present invention will be described below with reference to FIGS. 1 to 4.

Figure 1:
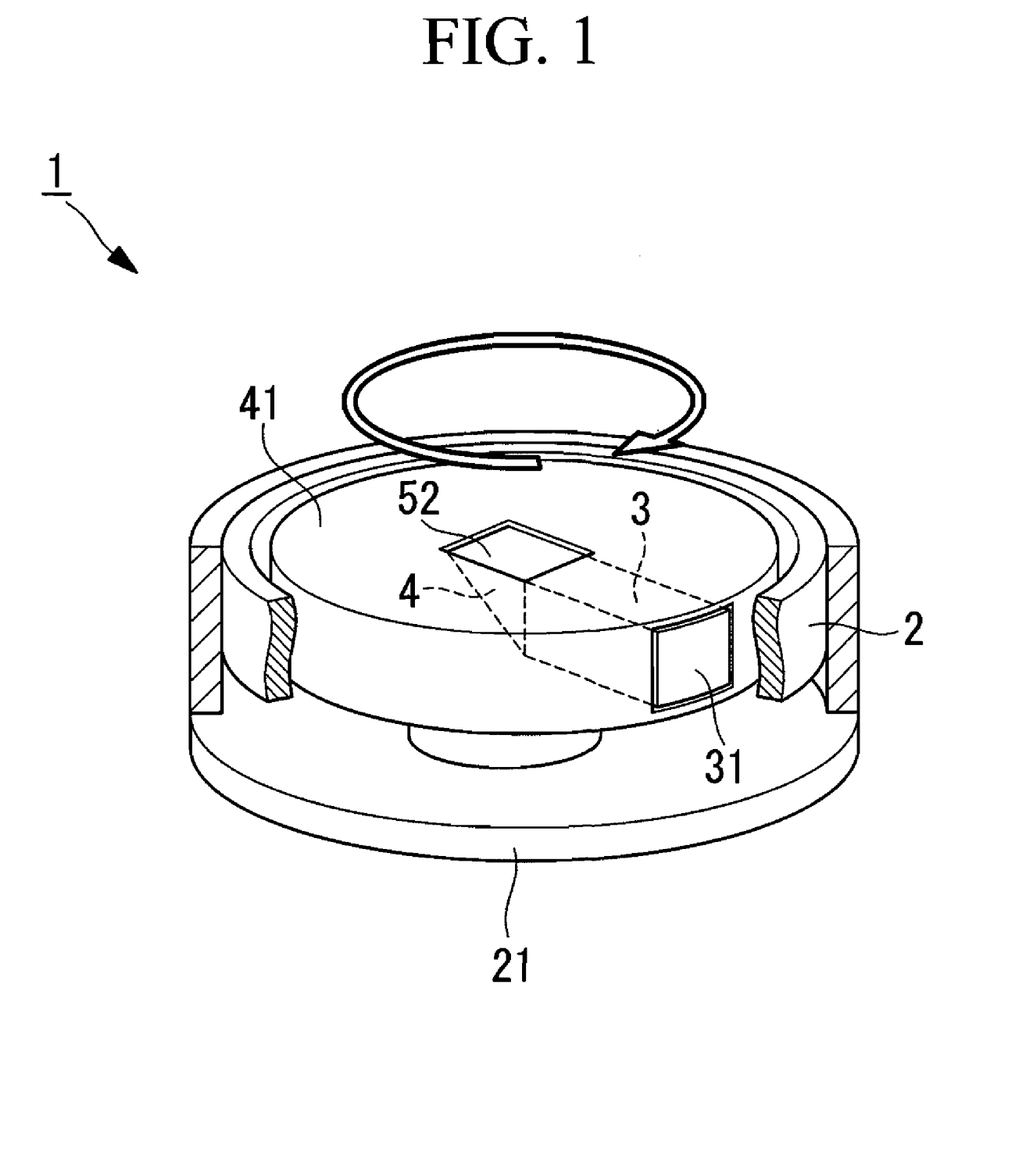
FIG. 1 is a schematic diagram for explaining, in outline, a light source apparatus of a first embodiment of the present invention.
Figure 2:
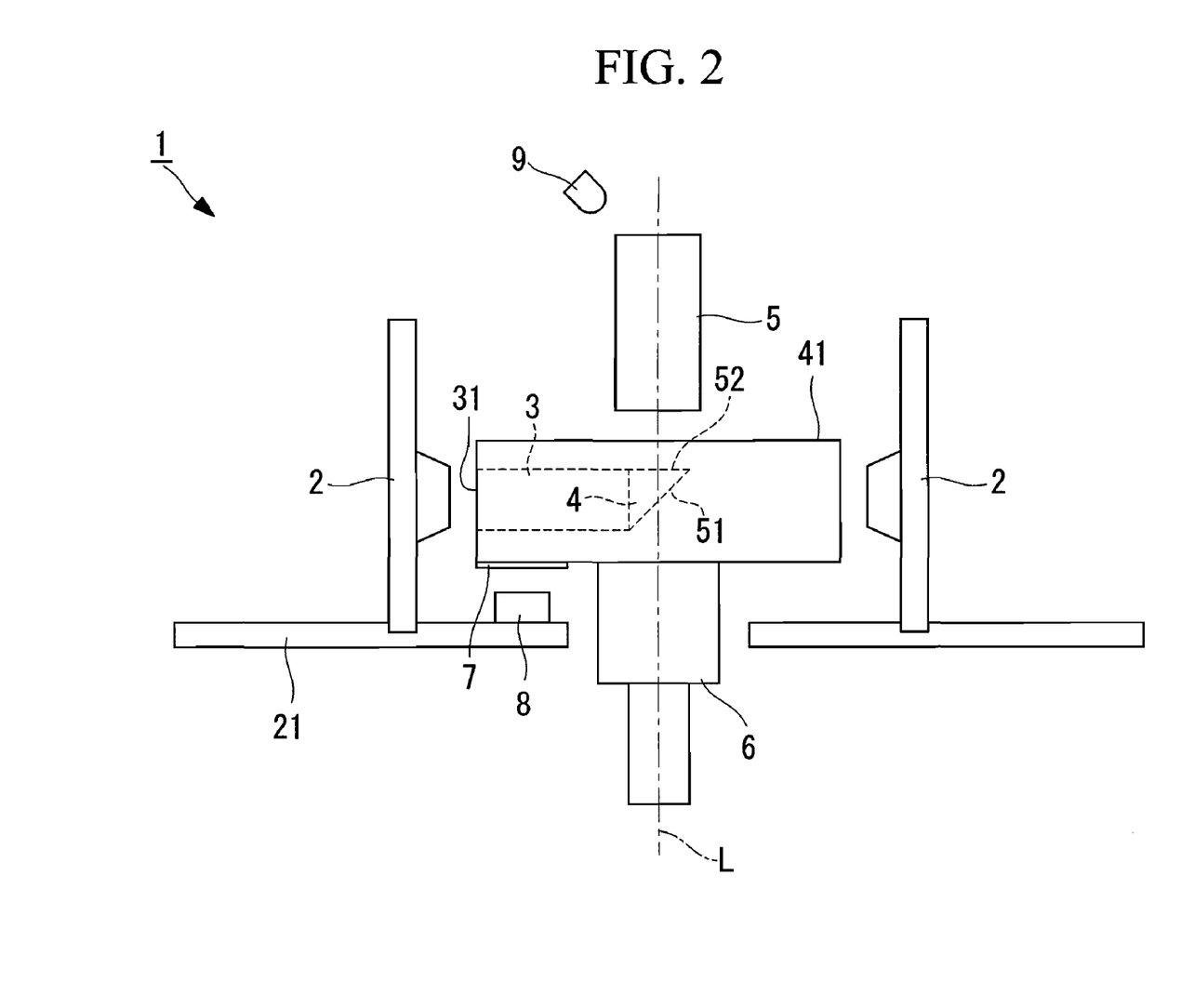
FIG. 2 is a sectional view for explaining the configuration of the light source apparatus of FIG. 1.

FIG. 1 is a schematic diagram for explaining, in outline, a light source apparatus of this embodiment. FIG. 2 is a sectional view for explaining the configuration of the light source apparatus of FIG. 1.

The light source apparatus 1 emits illumination light toward an illuminated region and is used as a light source for medical endoscopes, such as videoscopes, for example.

As shown in FIGS. 1 and 2, the light source apparatus 1 is provided with a plurality of LEDs (light source devices) 2 that emit illumination light; a light-guide rod (light-guide portion) 3, a reflecting prism (light-guide portion) 4, and a light guide 5 that guide the emitted illumination light to the illuminated region; a motor 6 that rotationally drives the light-guide rod 3 and the reflecting prism 4; a reflecting seal 7 and a rotation detection sensor 8 that detect the rotation phase of the light-guide rod 3 and the reflecting prism 4; and an optical sensor 9 that determines the light level of the emitted light.

Figure 3:
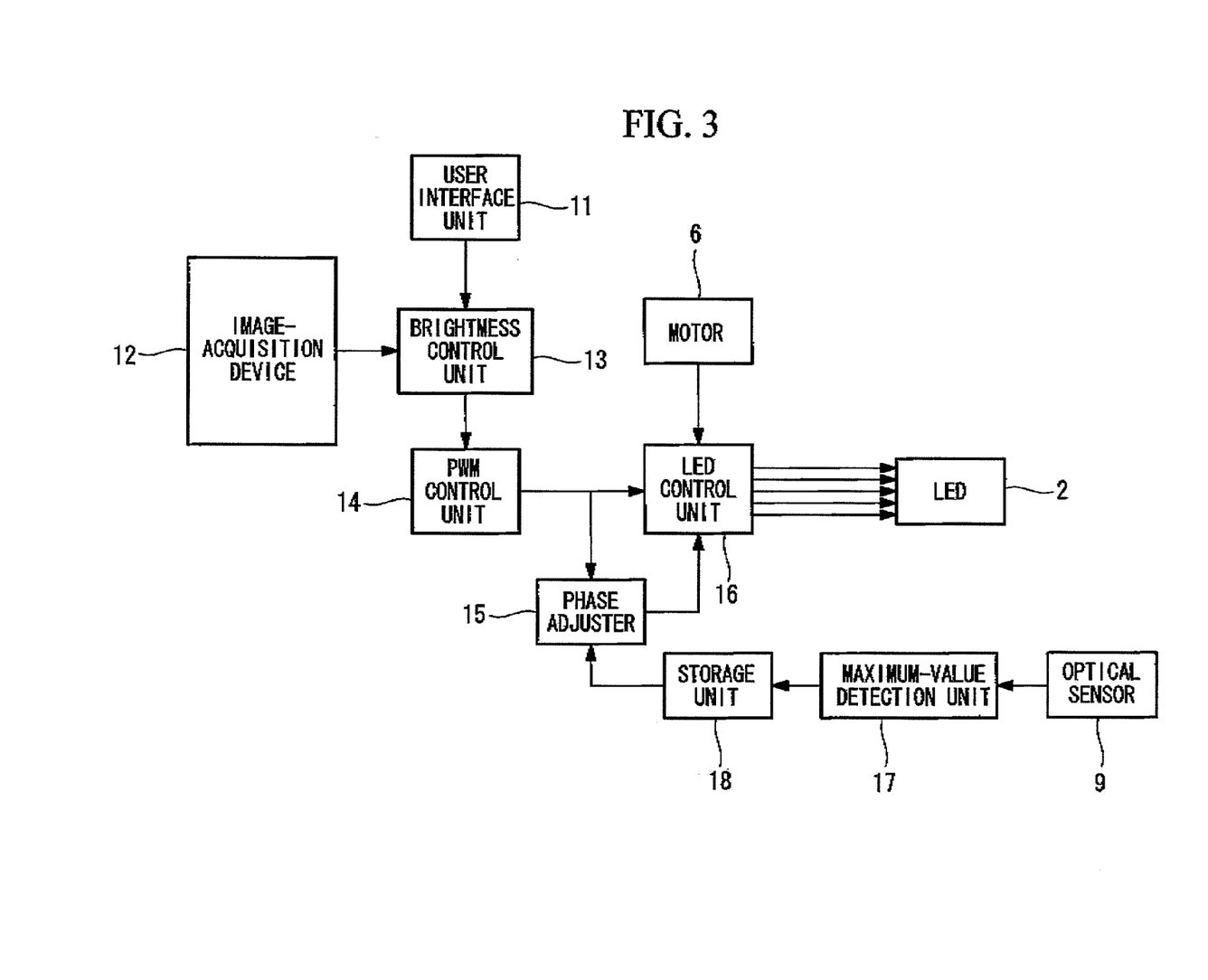
FIG. 3 is a block diagram for explaining control of the light source apparatus of FIG. 1.

FIG. 3 is a block diagram for explaining the control of the light source apparatus of FIG. 1.

Furthermore, as shown in FIG. 3, the light source apparatus 1 is provided with a user interface unit 11 where brightness instructions are input by the user, an image-acquisition device 12 that determines the light level of the reflected light reflected from the illuminated region, a brightness control unit 13 that decides the light level of the illumination light emitted from the light source apparatus 1, a PWM (Pulse Width Modulation) control unit 14 that controls the waveform of the current to be supplied to the LEDs 2, a phase adjuster (driving device) 15 that controls the lighting phase of the LEDs 2, an LED control unit 16 that controls the LEDs 2 on and off, a maximum-value detection unit 17 that detects the maximum value of the emitted light level, and a storage unit 18 that stores a compensation phase signal.

The LEDs 2 emit the illumination light, and the light level of the illumination light emitted therefrom is changed depending on the current supplied. As shown in FIGS. 1 and 2, the LEDs 2 are disposed side-by-side in the circumferential direction on an inner circumferential surface of a cylindrical supporting portion 21 and are disposed so as to emit the illumination light toward the central axis L of the supporting portion 21.

On the other hand, as shown in FIG. 3, lighting pulses from the LED control unit 16 for controlling the emission of the illumination light in the LEDs 2 are input to the LEDs 2.

As shown in FIGS. 1 and 2, the light-guide rod 3 is a rod lens that, together with the reflecting prism 4, guides the illumination light emitted from the LEDs 2 in the direction along the central axis L.

The light-guide rod 3 is a rod lens with a substantially rectangular cross section that extends in the radial direction centered on the central axis L. A light exit surface, which is a radially inward end portion of the light-guide rod 3, is disposed so as to face the reflecting prism 4, and a light entrance surface 31, which is a radially outward end portion, is disposed so as to face the LEDs 2. The light entrance surface 31 is a surface through which the illumination light emitted from the LEDs 2 enters the light-guide rod 3 and is taken into the light-guide rod 3.

A rod cover 41 that supports the light-guide rod 3 and the reflecting prism 4 is disposed around the light-guide rod 3.

As shown in FIGS. 1 and 2, the rod cover 41 is a cylindrical member inside of which the light-guide rod 3 and the reflecting prism 4 are disposed. The rod cover 41 is disposed such that the central line of the rod cover 41 coincides with the central axis L and is disposed so as to be rotatable about the central axis L.

Furthermore, a circumferential surface of the rod cover 41 has an opening formed therein that exposes the light entrance surface 31 of the light-guide rod 3, and a top surface of the rod cover 41 has an opening formed therein that exposes a light exit surface 52 of the reflecting prism 4.

The reflecting prism 4 is a prism that guides, together with the light-guide rod 3, the illumination light emitted from the LEDs 2 in the direction along the central axis L.

As shown in FIGS. 1 and 2, the reflecting prism 4 is a prism, which is formed in a shape of a triangle pole, having a light entrance surface that is disposed so as to face the light-guide rod 3, a reflecting surface 51 that reflects the incident illumination light, and the light exit surface 52 that is disposed so as to face the light guide 5.

The reflecting surface 51 of the reflecting prism 4 is disposed on the central axis L and is disposed so as to have an inclined angle of about 45° relative to the central axis L.

As shown in FIGS. 1 and 2, the light guide 5 guides the illumination light guided in the direction along the central axis L by the light-guide rod 3 and the reflecting prism 4 to the illuminated region.

The end surface of the light guide 5 at the reflecting prism 4 is disposed opposite the light exit surface 52 of the reflecting prism 4, and the illumination light emitted from the light exit surface 52 of the reflecting prism 4 is taken into the light guide 5 from the end surface. On the other hand, the end portion of the light guide 5 at the illuminated region extends toward the illuminated region, and the illumination light taken into the light guide 5 is emitted toward the illuminated region.

The motor 6 rotationally drives, together with the rod cover 41, the light-guide rod 3 and the reflecting prism 4 about the central axis L. The motor 6 is disposed on the under surface of the rod cover 41 such that the rotation axis coincides with the central axis L.

Furthermore, the motor 6 outputs rotational information or positional information of the motor 6 to the LED control unit 16. This rotational information or positional information is information related to, for example, the rotation phase or position of the light-guide rod 3.

The reflecting seal 7 detects, together with the rotation detection sensor 8, the rotation of the light-guide rod 3 and the reflecting prism 4 and reflects detection light, which is emitted from the rotation detection sensor 8 toward the rotation detection sensor 8.

The reflecting seal 7 is attached to a location facing the rotation detection sensor 8 in the radially outward region on the under surface of the rod cover 41.

The rotation detection sensor 8 detects, together with the reflecting seal 7, rotation of the light-guide rod 3 and the reflecting prism 4; and the rotation detection sensor 8 emits the detection light toward the reflecting seal 7 and detects the reflected detection light. In other words, the rotation detection sensor 8 is a reflective-type optical sensor that converts the level of the incident light to an electrical signal.

The rotation detection sensor 8 is disposed at a location opposite the region in the rod cover 41 where the reflecting seal 7 is attached on the underside of the rod cover 41.

On the other hand, a rotation signal of the light-guide rod 3 and the reflecting prism 4 is input to the LED control unit 16 from the rotation detection sensor 8.

As described above, the detection light reflected by the reflecting seal 7 may by detected by the rotation detection sensor 8 by arranging the reflecting seal 7, having higher light reflectance than that of the under surface of the rod cover 41, on the under surface of the rod cover 41, or conversely, the detection light reflected by the under surface of the rod cover 41 may by detected by the rotation detection sensor 8 by arranging a masking seal having lower light reflectance than that of the under surface of the rod cover 41 on the under surface of the rod cover 41; it is not particularly limited. In other words, with the rotation detection sensor 8, it is possible to detect an interruption, caused by the masking seal, in the reflection of the detection light by the under surface of the rod cover 41; it is not particularly limited.

The rotation detection sensor 8 is not limited to the above-described reflective-type sensor, and, it may be, for example, a transmissive sensor such as a photo-interrupter.

The optical sensor 9 determines the light level of the illumination light that has not entered the light guide 5 but has leaked, among the illumination light emitted from the reflecting prism 4.

The optical sensor 9 is disposed in the vicinity of the light exit surface 52 of the reflecting prism 4, and as shown in FIG. 3, the optical sensor 9 outputs the determined light-level signal to the phase adjuster 15.

The user interface unit 11 is a section where instructions related to the brightness of the illuminated region, in other words, the light level of the illumination light to be emitted toward the illuminated region, are input by the user.

The user interface unit 11 outputs a brightness setting signal to the brightness control unit 13.

The image-acquisition device 12 determines the light level of the illumination light emitted to the illuminated region by determining the light level of the reflected light reflected from the illuminated region.

The image-acquisition device 12 outputs the determined light-level signal to the brightness control unit 13.

The brightness control unit 13 decides the brightness of the illuminated region, in other words, the level of the light emitted from the LEDs 2. More specifically, the brightness control unit 13 controls the level of the light emitted from the LEDs 2 by increasing or decreasing it from the present level, on the basis of the brightness setting signal and the light-level signal.

The brightness setting signal and the light-level signal are input to the brightness control unit 13 from the user interface unit 11 and the image-acquisition device 12, respectively. On the other hand, the brightness control unit 13 outputs a brightness control signal decided by the PWM control unit 14.

The PWM control unit 14 generates a pulse-width signal for controlling the level of the light emitted from the LEDs 2 on the basis of the input brightness control signal.

The brightness control signal is input to the PWM control unit 14 from the brightness control unit 13. On the other hand, the PWM control unit 14 outputs the pulse-width signal to the phase adjuster 15 and the LED control unit 16.

The phase adjuster 15 controls the emission timing of the illumination light from the LED 2 on the basis of the compensation phase signal output from the maximum-value detection unit 17. In other words, the phase adjuster 15 controls the relative phase relationship between the LED 2 and the light-guide rod 3 when the illumination light is emitted from the LED 2.

The pulse-width signal is input to the phase adjuster 15 from the PWM control unit 14, and the compensation phase signal is input from the maximum-value detection unit 17 via the storage unit 18. On the other hand, the phase adjuster 15 outputs a phase signal to the LED control unit 16.

The LED control unit 16 controls the emission of the illumination light from a plurality of the LEDs 2. More specifically, the LED control unit 16 supplies pulsed current for lighting to the LEDs 2 on the basis of the pulse-width signal and the phase signal.

To the LED control unit 16, the pulse-width signal is input from the PWM control unit 14, the phase signal is input from the phase adjuster 15, and the rotation signal is input from the rotation detection sensor 8. On the other hand, the LED control unit 16 supplies the current for lighting to the LEDs 2.

A method for controlling the phase on the basis of the pulse width of the pulsed current to be supplied to the LEDs 2 will be described later.

The maximum-value detection unit 17 detects the maximum value of the light level emitted on the basis of the output of the optical sensor 9, and outputs the phase at that time as a compensation phase.

The light-level signal is input to the maximum-value detection unit 17 from the optical sensor 9. On the other hand, the maximum-value detection unit 17 outputs the compensation phase signal to the storage unit 18.

The storage unit 18 stores the compensation phase signal that is output from the maximum-value detection unit 17 and outputs the stored compensation phase signal to the phase adjuster 15.

Next, the emission control of the illumination light will be described after describing the emission path of the illumination light in the light source apparatus 1 of the above-described configuration.

As shown in FIGS. 1 and 2, when the illumination light is emitted from the light source apparatus 1, the motor 6 rotationally drives the rod cover 41 and also rotationally drives the light-guide rod 3 and the reflecting prism 4.

The pulsed current is supplied synchronously with the rotation of the light-guide rod 3 to a plurality of the LEDs 2 disposed on the inner circumferential surface of the supporting portion 21. When the current is supplied to the LEDs 2 in a pulsed fashion, the LEDs 2 emit the illumination light in a pulsed fashion corresponding to the supply of the current. More specifically, the LEDs 2 emit the illumination light only when the light entrance surface 31 of the light-guide rod 3 is passing in front of each LED 2, in other words, when the light exit surface of the LED 2 and the light entrance surface 31 of the light-guide rod 3 face each other.

Therefore, the illumination light enters the light-guide rod 3 from a plurality of the LEDs 2 continuously or intermittently.

At this time, a large current compared with the current in the case where the current is steadily supplied to the LEDs 2, in other words, the maximum rated current is supplied. Therefore, in comparison with the case where the current is being steadily supplied, illumination light with a high light level is emitted from the LEDs 2.

It is desirable that the current value being supplied to the LEDs 2 is such that the time-averaged value of the current supplied in a pulsed fashion does not exceed the time-averaged value of the maximum rated current. By doing so, the LEDs 2 are prevented from experiencing damage and deterioration.

The illumination light emitted from the LEDs 2 is taken into the light-guide rod 3 from the light entrance surface 31 and propagates within the light-guide rod 3 toward the central axis L. The illumination light propagated within the light-guide rod 3 enters the reflecting prism 4 from the light-guide rod 3 and is reflected by the reflecting surface 51 in the direction along the central axis L. The illumination light reflected by the reflecting surface 51 is emitted from the light exit surface 52 of the reflecting prism 4 and enters the light guide 5 disposed opposite thereto. The illumination light that has entered the light guide 5 is guided to the illuminated region by the light guide 5 and is emitted toward the illuminated region.

Next, the emission control of the illumination light, which is the feature of this embodiment, will be described.

A compensation phase value is first acquired as described below before the illumination light is emitted to the illuminated region from the light source apparatus 1.

As shown in FIGS. 2 and 3, lighting of the LEDs 2 is inhibited by the LED control unit 16 until the rotating speed of the motor 6 reaches the predetermined rotating speed and the rotating speed is stabilized after the light source apparatus 1 has been activated. In other words, the LED control unit 16 monitors the rotational information or the positional information input from the rotation detection sensor 8, and allows the LEDs 2 to be lit once the rotating speed of the motor 6 has reached a stable rotating speed, that is, the predetermined rotating speed.

More specifically, when the rod cover 41 is rotated by the motor 6, the rotation of the rod cover 41 is detected by the rotation detection sensor 8. In other words, when the reflecting seal 7 passes in front of the rotation detection sensor 8, the output level of the rotation detection sensor 8 is changed.

The output of the rotation detection sensor 8 is input to the LED control unit 16 as rotational information and positional information of the light-guide rod, which have been converted to an electrical signal by the rotation detection sensor 8.

Once the rotating speed of the motor 6 is stabilized, the LED control unit 16 supplies current to one of the LEDs 2 continuously to cause the illumination light to be emitted continuously.

The illumination light emitted from the LED 2 is taken into the light-guide rod 3 only when the light entrance surface 31 of the light-guide rod 3 is positioned opposite the one LED 2.

In other words, the illumination light is emitted from the light exit surface 52 via the light-guide rod 3 and the reflecting prism 4 only when the light-guide rod 3 passes in front of the one LED 2 emitting the illumination light, and the illumination light is not emitted from the light exit surface 52 during the other period.

The light level of the illumination light emitted from the light exit surface 52 becomes the maximum when the one LED 2 and the light entrance surface 31 are directly opposed to each other, and the light level decreases as the light entrance surface 31 shifts from the directly opposed position.

The light level of part of the illumination light emitted from the light exit surface 52, in other words, the light that has leaked and not been taken into the light-guide rod 3, is detected by the optical sensor 9. The optical sensor 9 outputs the light-level signal regarding the detected light level of the illumination light, and the light-level signal is input to the maximum-value detection unit 17.

The maximum-value detection unit 17 detects the phase of the light-guide rod 3 with which the light-level signal becomes the maximum, in other words, the phase of the light-guide rod 3 where the one LED 2 and the light entrance surface 31 are directly opposed to each other, and outputs the phase to the storage unit 18 as the compensation phase value.

Acquisition of the compensation phase value is thus completed as described above.

By doing so, acquisition of the compensation phase value is completed simply by rotating the light-guide rod 3 once, and acquisition of the compensation phase value can thus be performed quickly.

This acquisition of the compensation phase value need only be performed at the time of delivery of the light source apparatus 1, and the compensation phase value stored in the storage unit 18 may be used thereafter, or, acquisition of the compensation phase value may be performed every time the light source apparatus 1 is used; it is not particularly limited.

When acquisition of the compensation phase value is performed only at the time of delivery, the optical sensor 9 and the maximum-value detection unit 17 may be disposed on the light source apparatus 1 in a detachable manner. By doing so, after the compensation phase value has been acquired, the optical sensor 9 and the maximum-value detection unit 17 can be detached from the light source apparatus 1. The compensation phase value stored in the storage unit 18 is used.

When acquisition of the compensation phase value is performed every time the light source apparatus 1 is used, the light source apparatus 1 need not be provided with the storage unit 18.

In addition, instead of using a dedicated sensor such as the optical sensor 9, the phase compensation may be performed by detecting the light level of the illumination light emitted from the light exit surface 52 by using an image-acquisition unit of a videoscope in which the light source apparatus 1 is used.

As described above, it is possible to detect a phase with which the light level detected by the optical sensor 9 becomes the maximum, or to detect a phase that corresponds to the center of gravity of the light-level area in a graph showing the changes of the light level against phase, with the vertical axis indicating the light level and the horizontal axis indicating the phase; it is not particularly limited.

As described above, the compensation phase value may be acquired by continuously emitting the illumination light from the one LED 2, or, the compensation phase value may be acquired by emitting the pulsed illumination light from the LEDs 2 and changing the timing at which the illumination light is emitted; it is not particularly limited.

More specifically, once the rotating speed of the motor 6 is stabilized, the LED control unit 16 supplies the pulsed current to the LEDs 2 to emit the illumination light from the LEDs 2 with the maximum pulse width.

Here, the maximum pulse width means the maximum pulse width with which the illumination light can be made incident on the light entrance surface 31 of the rotating light-guide rod 3. In other words, the maximum pulse width means the range between the point at which the one end of the light entrance surface 31 arrived at the light exit surface of the illumination light of the LED 2 and the point at which the other end of the light entrance surface 31 passed the light exit surface of the illumination light of the LED 2; and means the maximum range with which the illumination light can be taken into the light entrance surface 31 of the light-guide rod 3.

Thereafter, the phase adjuster 15 changes the timing at which the illumination light is emitted from the LEDs 2, and the light level of a part of the illumination light emitted from the light exit surface 52 is detected by the optical sensor 9.

In other words, the phase adjuster 15 changes the rotation phase of the light-guide rod 3 when the illumination light is emitted in a pulsed fashion from the LEDs 2 from 0 to $2\pi$, in every revolution of the light-guide rod 3, and the change of the illumination light emitted from the light exit surface 52 is detected.

The light-level signal related to the light level detected by the optical sensor 9 is input to the maximum-value detection unit 17. The maximum-value detection unit 17 detects the phase with which the light-level signal becomes the maximum, and outputs the phase to the storage unit 18 as the compensation phase value.

Acquisition of the compensation phase value is completed as described above.

By doing so, since acquisition of the compensation phase value is performed under the same conditions as the actual emission of the illumination light to the illuminated region, a more accurate compensation phase value can be acquired. In other words, it is possible to acquire the compensation phase value under conditions that include variations of the rotation phase of the motor 6 and so forth.

Next, the emission control of the illumination light on the basis of the acquired compensation phase value will be described.

Similarly to acquisition of the compensation phase value, the lighting of the LEDs 2 is first inhibited by the LED control unit 16 until the rotating speed of the motor 6 reaches the predetermined rotating speed and the rotating speed is stabilized after the light source apparatus 1 has been activated.

Once the rotation of the motor 6 is stabilized, the LED control unit 16 supplies current to the LED 2 that faces the light entrance surface 31 of the light-guide rod 3 on the basis of the compensation phase value stored in the storage unit 18 and the output of the rotation detection sensor 8 to cause the illumination light to be emitted.

More specifically, when the output level of the rotation detection sensor 8 that is input to the LED control unit 16 is changed, in other words, when the reflecting seal 7 passes in front of the rotation detection sensor 8, the LED control unit 16 supplies current to the LED 2 that faces the light entrance surface 31 of the light-guide rod 3 to cause the illumination light to be emitted in a pulsed fashion.

When the rotational period of the motor 6 rotating at a constant rotating speed is indicated by $\lambda$ and the number of LEDs 2 disposed in the circumferential direction is indicated by N, the LED control unit 16 supplies the pulsed current to the LEDs 2 every $\lambda/N$ time in sequence in the direction of rotation of the motor 6.

By doing so, the illumination light emitted from the plurality of the LEDs 2 in a pulsed fashion is incident on the light entrance surface 31 of the light-guide rod 3 sequentially.

Next, a control method of the light level of the illumination light emitted from the light source apparatus 1 will be described.

When the light level of the illumination light is to be controlled, as shown in FIG. 3, the user inputs to the user interface unit 11 an instruction for setting the brightness, and a brightness setting signal for setting the brightness is input to the brightness control unit 13 from the user interface unit 11.

On the other hand, the image-acquisition device 12 detects the light level of the reflected light reflected from the illuminated region that is being illuminated by the light source apparatus 1, and the luminance signal of the illuminated region is input to the brightness control unit 13.

The brightness control unit 13 decides whether the light level of the illumination light emitted from the light source apparatus 1 is to be increased or decreased from the present level based on the difference between the input brightness setting signal and the luminance signal. Then, the brightness control unit 13 outputs the brightness control signal that controls the light level of the illumination light emitted from the light source apparatus 1 to the PWM control unit 14 on the basis of the decision.

More specifically, when the brightness of the illuminated region that is being illuminated by the light source apparatus 1 is darker than the brightness assigned by the user, in other words, when the brightness related to the luminance signal is darker than the brightness related to the brightness setting signal, the brightness control unit 13 outputs the brightness control signal for increasing the light level of the illumination light currently being emitted.

The brightness control signal is input to the PWM control unit 14, and the PWM control unit 14 outputs the pulse-width signal that corresponds to the brightness control signal to the LED control unit 16 and the phase adjuster 15.

The phase adjuster 15 outputs the phase signal that controls the phase at which the illumination light is emitted from the LEDs 2 on the basis of the compensation phase value input from the storage unit 18.

Figure 4:
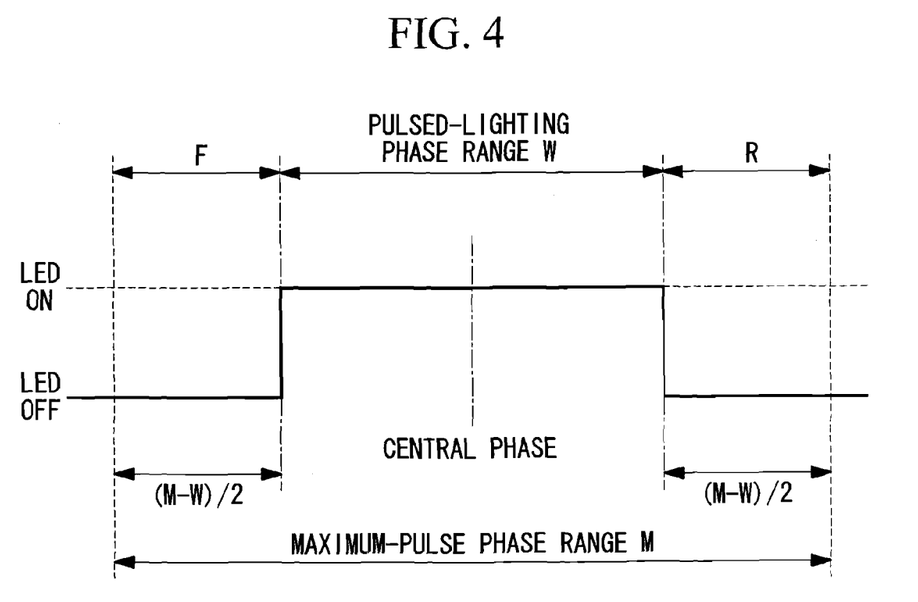
FIG. 4 is a graph for explaining emission control of illumination light when control of the light level of the illumination light is performed by the light source apparatus of FIG. 1.

For example, when the light level of the illumination light emitted from the light source apparatus 1 is decreased, a pulsed-lighting phase period during which the illumination light is emitted from the LEDs 2 becomes shorter than the maximum pulsed-lighting phase period. In other words, a pulsed-lighting phase range W with which the illumination light is emitted from the LEDs 2 becomes shorter than a maximum-pulse phase range M.

Furthermore, depending on the decreased level of the pulsed-lighting phase range, the emission timing of the illumination light, in other words, the phase with which the illumination light is emitted, is delayed to match the central phase of the pulsed-lighting phase range W and the central phase of the maximum-pulse phase range M. In other words, even if the pulsed-lighting phase range fluctuates at this time, the central phase of the pulsed-lighting phase range W is fixed to the central phase of the maximum-pulse phase range M.

FIG. 4 is a graph for explaining the emission control of the illumination light when control of the light level of the illumination light is conducted by the light source apparatus of FIG. 1. In FIG. 4, the horizontal axis indicates the rotation phase of the light-guide rod, and the vertical axis indicates the light level of the illumination light emitted.

More specifically, in the pulsed-lighting phase range W, as shown in FIG. 4, the illumination light is emitted at a phase delayed by (M−W)/2 relative to the phase with which the illumination light is emitted in the maximum-pulse phase range M.

At this time, a preceding light-out phase range F and a succeeding light-out phase range R having the phase range of (M−W)/2 are formed before and after the pulsed-lighting phase range W, respectively. In the preceding light-out phase range F and succeeding light-out phase range R, the illumination light is not emitted.

By doing so, even if the pulsed-lighting phase range fluctuates, the central phase of the pulsed-lighting phase range W is fixed to the central phase of the maximum-pulse phase range M.

With the configuration described above, by controlling the pulsed-lighting phase range W, it is possible to adjust the light level of the illumination light emitted through the light-guide rod 3 and the reflecting prism 4 by adjusting the period during which the illumination light is emitted from the LED 2. Therefore, it is possible to suppress changes in the color temperature of the emitted illumination light compared with a method in which the value of the current to be supplied to the LEDs 2 is adjusted.

Furthermore, even if the pulsed-lighting phase range W is shortened to shorten the period during which the illumination light is emitted from the LED 2, because the preceding light-out phase range F and the succeeding light-out phase range R, in which the LED 2 is turned off, are ensured before and after the pulsed-lighting phase range W, the illumination light emitted from the LED 2 is incident on the light entrance surface 31 of the light-guide rod 3.

In other words, even if a variation is caused between the rotation phase of the light-guide rod 3 and the phase with which the illumination light is emitted in the LEDs 2, the above-described variation is absorbed by the preceding light-out phase range F and the succeeding light-out phase range R; therefore, the illumination light emitted from the LED 2 is incident on the light entrance surface 31 and is emitted toward the illuminated region.

Therefore, it is possible to suppress light level fluctuation of the emitted illumination light resulting from the fluctuation of the rotational period of the motor 6 and so forth, and to prevent the perception of flickering.

By performing control on the basis of the acquired compensation phase value, it is possible to ensure the preceding light-out phase range F and the succeeding light-out phase range R of substantially equal duration before and after the pulsed-lighting phase range W in which the illumination light is emitted.

In other words, since the light entrance surface 31 of the light-guide rod 3 passes in front of the LEDs 2 continuously emitting light, the light level of the illumination light emitted through the light-guide rod 3 and the reflecting prism 4 changes according to the rotation phase of the light-guide rod 3 and the reflecting prism 4. By setting the phase corresponding to the maximum value of the light level at this time as the central phase of the maximum-pulse phase range M, or, by setting the phase corresponding to the center of gravity of the area of the light level as the central phase of the maximum-pulse phase range M, it is possible to set the preceding light-out phase range F and the succeeding light-out phase range R to substantially equal widths.

Therefore, the illumination light emitted from the LEDs 2 can be made incident on the light entrance surface 31, whether the variation between the rotation phase of the light-guide rod 3 and the reflecting prism 4 and the phase with which the illumination light is emitted in the LED 2 is toward the advanced side of the emission phase of the illumination light or toward the delayed side of the emission phase of the illumination light.

Since the illumination light is emitted from the LEDs 2 in a pulsed fashion, it is possible to achieve illumination light with a high light level compared with the case where the illumination light is emitted steadily from the LEDs 2. Furthermore, since a plurality of the LEDs 2 are provided, and the illumination light emitted toward the central axis L direction is guided to the illuminated region by the light-guide rod 3 and the reflecting prism 4, it is possible to achieve illumination light with a high light level continuously.

Since the pulsed-lighting phase range W is controlled on the basis of the light level detected by the optical sensor 9, regardless of the emission characteristics of the illumination light by the LEDs 2, it is possible to maximize the light level of the illumination light emitted from the light-guide rod 3.

In other words, by performing control on the basis of the light level detected by the optical sensor 9, it is possible to set the preceding light-out phase range F and the succeeding light-out phase range R before and after the pulsed-lighting phase range W. Therefore, the illumination light emitted from the LEDs 2 can be made incident on the light entrance surface of the light-guide rod 3 reliably.

Second Embodiment

Next, a second embodiment of the present invention will be described with reference to FIG. 5.

The basic configuration of the light source apparatus of this embodiment is the same as the first embodiment, but the emission control method of the illumination light differs from that in the first embodiment. Therefore, in this embodiment, only the emission control method of the illumination light will be described using FIG. 5, and a description of other structural elements and so forth will be omitted.

Figure 5:
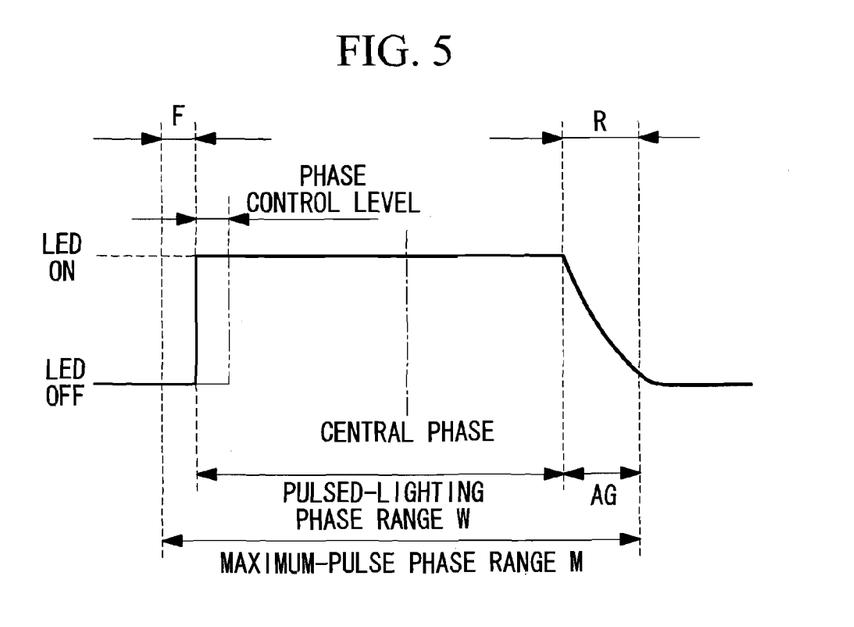
FIG. 5 is a graph for explaining emission control of illumination light when control of the light level of illumination light is performed by a light source apparatus of a second embodiment of the present invention.

FIG. 5 is a graph for explaining the emission control of the illumination light when control of the light level of the illumination light is performed by the light source apparatus in this embodiment. In FIG. 5, the horizontal axis indicates the rotation phase of the light-guide rod and the vertical axis indicates the light level of the illumination light emitted.

The configuration of the light source apparatus 1 and the emission path of the illumination light in this embodiment are the same as the configuration and the emission path of the illumination light in the first embodiment, and a description thereof will be omitted.

Next, the emission control of the light level of the illumination light, which is the feature of this embodiment, will be described with reference to FIGS. 3 and 5.

Processes from the input of the instruction for setting the brightness to the user interface unit 11 by user to the output of the pulse-width signal corresponding to the brightness control signal to the LED control unit 16 and the phase adjuster 15 from the PWM control unit 14 are the same as in the first embodiment, and descriptions thereof will be omitted.

As shown in FIG. 3, the phase adjuster 15 outputs the phase signal that controls the phase with which the illumination light is emitted from the LEDs 2 on the basis of the compensation phase value input from the storage unit 18 and the light level detected by the optical sensor 9.

For example, when the light level of the illumination light emitted from the light source apparatus 1 is decreased, the pulsed-lighting phase period W during which the illumination light is emitted from the LEDs 2 becomes shorter than the maximum-pulse phase period M. In other words, the pulsed-lighting phase range W with which the illumination light is emitted from the LEDs 2 becomes shorter than the maximum-pulse phase range M.

Furthermore, as shown in FIG. 5, depending on the decreased level of the pulsed-lighting phase range and the light level detected by the optical sensor 9, the phase adjuster 15 delays the emission timing of the illumination light, in other words, the phase with which the illumination light is emitted. More specifically, the phase adjuster 15 delays the phase with which the illumination light is emitted such that the light level detected by the optical sensor 9 becomes the maximum.

As shown in FIG. 5, even in a succeeding light-out phase period R during which the current supply to the LEDs 2 is stopped after the pulsed-lighting phase period W, a persistent period AG during which the illumination light is emitted from the LEDs 2 exists. If the central phase of the pulsed-lighting phase range W and the central phase of the maximum-pulse phase range M are matched as in the first embodiment, the persistent period AG exceeds the maximum-pulse phase range M.

Thus, by advancing the phase of the pulsed-lighting phase period W by making the preceding light-out phase range F shorter and the succeeding light-out phase range R longer on the basis of the light level detected by the optical sensor 9, the persistent period AG exceeding the maximum-pulse phase range M comes to be included within the maximum-pulse phase range M. In other words, the illumination light emitted during the persistent period AG is also incident on the light entrance surface 31 of the light-guide rod 3.

When this light level detected by the optical sensor 9 becomes the maximum, the central phase in the maximum-pulse phase range M and the phase corresponding to the center of gravity of the light-level area in the graph showing the change of the light level against the phase, with the vertical axis indicating the light level and the horizontal axis indicating the phase, are matched.

With the configuration described above, the succeeding light-out phase range R becomes longer then the preceding light-out phase range F. Therefore, even there is the persistent period AG during which the illumination light is emitted from the LEDs 2 even after the supply of the current to the LEDs 2 has been shut off, it becomes easier for the illumination light related to the persistent period AG to be made incident on the light entrance surface 31, and thus, the light level of the illumination light emitted toward the illuminated region becomes large.

The invention claimed is:

1. A light source apparatus comprising:
   a plurality of light source devices that are disposed in a form of a ring and that emit illumination light toward a central axis of the ring by being lit in a sequential pulsed fashion;
   a light-guide portion having a light entrance surface that is rotatably disposed on the central axis and on which the illumination light emitted from the light source devices is incident, and a reflecting surface that reflects the incident illumination light in the direction along the central axis; and
   a driving device that controls a pulsed-lighting phase range, which is a period during which the light source devices are lit according to a rotation phase of the light-guide portion;
   wherein by making a phase of a center of gravity of a light level related to a change of the light level of the illumination light emitted from the light-guide portion to become substantially a center of a maximum-pulse phase range when the light-guide portion is rotated under a condition where one of the light source device is made to emit light continuously, the driving device controls the pulsed-lighting phase range such that, when the pulsed-lighting phase range is shorter than the maximum-pulse phase range, which is a longest period during which the illumination light emitted from the light source devices is incident on the light entrance surface, a preceding light-out phase range and a succeeding light-out phase range, which are periods during which the light source devices are turned off, are provided before and after the pulsed-lighting phase range in the maximum-pulse phase range.

2. A light source apparatus according to claim 1, wherein the driving device controls the pulsed-lighting phase range such that the preceding light-out phase range and the succeeding light-out phase range have substantially equal widths.

3. A light source apparatus according to claim 2, further comprising an optical sensor that detects the light level of the illumination light emitted from the light-guide portion,
   wherein the driving device controls the pulsed-lighting phase range such that the light level detected by the optical sensor becomes a maximum.

4. A light source apparatus according to claim 1, wherein the driving device controls the pulsed-lighting phase range such that the succeeding light-out phase range becomes longer than the preceding light-out phase range.

5. A light source apparatus according to claim 4, further comprising an optical sensor that detects the light level of the illumination light emitted from the light-guide portion,
   wherein the driving device controls the pulsed-lighting phase range such that the light level detected by the optical sensor becomes a maximum.

6. A light source apparatus according to claim 1, further comprising an optical sensor that detects the light level of the illumination light emitted from the light-guide portion,
   wherein the driving device controls the pulsed-lighting phase range such that the light level detected by the optical sensor becomes the maximum.

* * * * *